United States Patent [19]
Borland et al.

[11] Patent Number: 5,912,163
[45] Date of Patent: Jun. 15, 1999

[54] HIGH FLOW TECHNIQUE FOR HARVESTING MAMMALIAN CELLS

[75] Inventors: Kermit M. Borland, Shrewsbury; Barbara A. Chandler, Lexington; Dianna Hunt Picton, Bedford; Shawn P. Cain, North Chelmsford; Deborah Deane, Orange; Claudy J.P. Mullon, Framingham, all of Mass.

[73] Assignee: Circe Biomedical, Inc., Lexington, Mass.

[21] Appl. No.: 08/953,541

[22] Filed: Oct. 20, 1997

[51] Int. Cl.$^6$ .............................. C07G 15/00; A01N 1/02
[52] U.S. Cl. .............................. 435/268; 435/1.1; 435/1.2
[58] Field of Search ................................ 435/1.1, 1.2, 268

[56] References Cited

PUBLICATIONS

Gerlach et al., "High Yield Hepatocyte Isolation from Pig Livers for Investigation of Hybrid Liver Support Systems: Influence of Collagenase Concentration and Body Weight", J. Surgical Res. 62: 85–9 (1996).

Gerlach et al., "Comparison of Four Methods for Mass Hepatocyte Isolation from Pig and Human Livers", Transplantation 57(9): 1318–22 (1994).

Gerlach et al., "Nonenzymatic versus enzymatic hepatocyte isolation from pig livers for larger scale investigations of liver cell perfusion systems," *Intl. J. Artificial Organs,* 16(9):677–681, 1993.

Koebe et al., "Porcine Hepatocytes for Biohybrid Artifical Liver Devices: A Comparison of Hypothermic Storage Techniques," *Artif. Organ,* 20(11):1181–1190, 1996.

Koebe and Schildberg, "Isolation of porcine hepatocytes from slaughterhouse organs," *Intl. J. Artificial Organs,* 19(1):53–60, 1996.

Morsiani et al., "Automatic Liver Cell Processing Facilitates Large Scale Isolation and Purification of Porcine Hepatocytes," *ASAIO Journal,* 41:155–161, 1994.

Naik et al., "Isolation and Culture of Porcine Hepatocytes for Artificial Liver Support," *Cell Transplantation,* 5(1):107–115, 1996.

Seglen, "Preparation of Isolated Rat Liver Cells," Norsk Hydro's Institute for Cancer Research, Department of Tissue Culture, The Norwegian Raidum Hospital, Montebello, Oslo, Norway, 29–83, 1976.

Sielaff et al., "A Technique for Porcine Hepatocyte Harvest and Description of Differentiated Metabolic Functions in Static Culture," U. Minnesota Medical School, Coon Rapids, MN 1995.

*Primary Examiner*—Sandra E. Saucier
*Attorney, Agent, or Firm*—Fish & Richardson, P.C.

[57] ABSTRACT

The invention is based in part on the observation that significant portions of porcine livers appear to remain intact after perfusion by standard methods, suggesting that the perfusion procedures employed do not result in complete enzymatic digestion. Recovery of cells is therefore substantially lower than would be possible if the organs were thoroughly digested. It is found that increased perfusion flow rate, occlusion of at least one major blood vessel leading out of the organ, increased enzymatic digestion time, and vigorous tissue dissociation techniques can be combined to afford a uniquely high yield of viable cells.

21 Claims, 1 Drawing Sheet

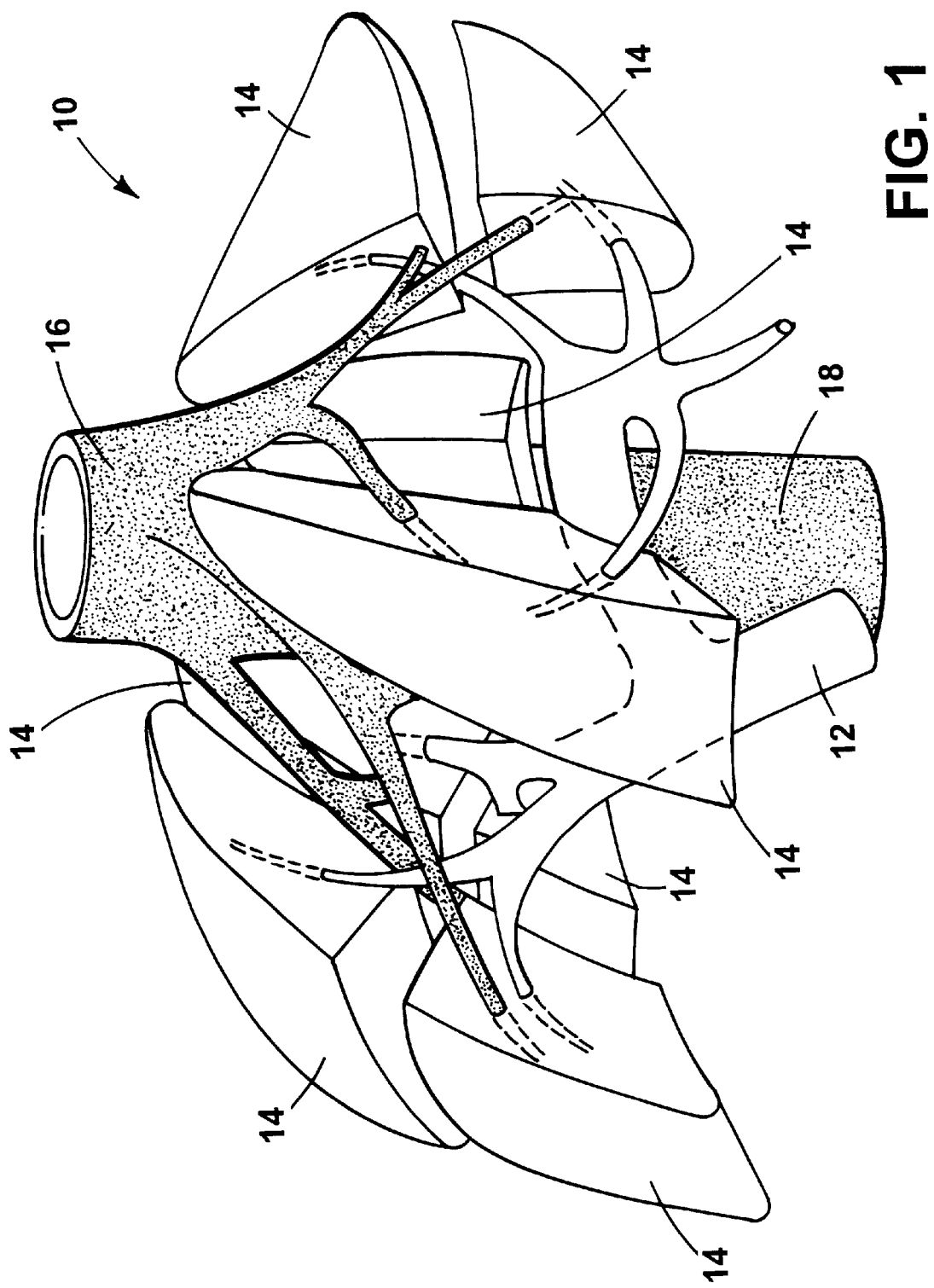

HIGH FLOW TECHNIQUE FOR HARVESTING MAMMALIAN CELLS

BACKGROUND OF THE INVENTION

The isolation of cells from mammalian organs has wide-ranging application in medicine, as isolated cells can be manipulated and used for producing chemicals, for degrading chemicals, or in medical devices, such as artificial organs. To achieve these goals, it is important that cells can be isolated in high yield and in relatively the same relative proportions as they exist in the organ.

For example, a liver from a pig weighing approximately 30 pounds typically weighs about 535 grams and encompasses a minimum of about $45 \times 10^9$ hepatocyte cells. The cell recovery from standard procedures for isolating hepatocytes from porcine livers averages only about $14 \times 10^9$ viable cells, however, with a viability of 89% per liver (IND-Bioartificial Liver and Perfusion Circuit, Vol. II, Section 7.D). The standard procedures entail pumping various buffers through the vascular network of the organ. This process is called perfusion. The buffers are necessary for maintaining the viability of the cells after the host animal has been euthanized. An enzyme breaks down connective tissue within the organ that serves to keep the organ intact and the relative position of the cells fixed within the organ during the life of the host.

Additionally, the relative proportions of cells from the different zones of the organ are often highly variable among the cells isolated by use of the standard methods when all lobes of the liver do not digest completely. Since the cells from each of the various zones often have different properties and activity, the bulk properties of the cells isolated by the standard methods can vary greatly.

SUMMARY OF THE INVENTION

The invention is based in part on the observation that significant portions of porcine livers appear to remain intact after perfusion by standard methods, suggesting that the perfusion procedures employed do not result in complete enzymatic digestion. Recovery of cells is therefore substantially lower than would be possible if the organs were thoroughly digested. It is found that increased perfusion flow rate, occlusion of at least one major blood vessel leading out of the organ, increased enzymatic digestion time, and vigorous tissue dissociation techniques can be combined to afford a uniquely high yield of viable cells.

In general, the invention features a method of collecting cells such as hepatocytes from a mammalian organ such as a liver (e.g., a porcine liver). The method includes the steps of cannulating a blood vessel leading to the organ to produce an input line for the introduction of a fluid; occluding all but one remaining blood vessel leading to or from the organ, such that the non-occluded vessel constitutes an output line for the egress of the fluid; digesting the organ with a continuous flow of collagenase buffer in through the input line and out through the output line; dissociating the digested organ; and placing the dissociated organ on a sieve. The sieve contains a layer of beads that mechanically separate the cells from the remainder of the organ.

The invention also features a second method of collecting cells such as hepatocytes from a mammalian organ such as a liver (e.g., a porcine liver). The second method includes the steps of cannulating a blood vessel leading to the organ to produce an input line for the introduction of fluids; occluding all but one remaining blood vessel leading to or from the organ, such that the non-occluded vessel constitutes an output line for the egress of the fluids; digesting the organ with a continuous flow of collagenase buffer introduced via the input line and evacuated via the output line; massaging the organ concurrent with the digesting step to enhance perfusion; dissociating the digested organ; and passing the dissociated organ through a sieve to separate the cells from the connective tissue of the organ. The sieve can contain a layer of beads.

The invention features a third method of collecting cells such as hepatocytes from a mammalian organ such as a liver (e.g., a porcine liver). The third method includes the steps of cannulating a blood vessel leading to the organ to produce an input line for the introduction of fluids; occluding all but one remaining blood vessel leading to or from the organ, such that the non-occluded vessel constitutes an output line for the egress of the fluids; digesting the organ with a continuous flow of collagenase buffer introduced via the input line and evacuated via the output line; periodically and momentarily blocking the output line during the digesting step to increase the pressure within the organ; manually dissociating the digested organ; and passing the crushed organ through a sieve to separate the cells from the connective tissue of the organ. The sieve can contain a layer of beads.

The method can also include the step of massaging the organ concurrent with the digesting step to enhance perfusion.

The host can be any mammal such as a primate, horse, cow, pig, sheep, goat, dog, cat, mouse, rat, guinea pig, hamster, or ferret. Although a human could theoretically serve as a host, removal of an organ generally necessitates sacrifice of the host.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

An advantage of the new methods is that the yield of viable cells can be dramatically improved without the need for additional equipment or radically different procedures. Since the methods afford greater cell recovery, fewer animals need to be sacrificed to obtain cells for research or in the manufacture of artificial organs, for example. Moreover, the more cells that are harvested per liver, the lower the per lot costs associated with quality control can be.

Another advantage of the new methods is that the cells isolated by using the new procedures can have more consistent bulk properties than do the cells isolated by the traditional methods. For example, the hepatocytes from any given zone of the liver can perform different roles and have different activity from those from other zones; the liver is therefore said to have a "heterogeneous hepatocyte population." Although the relative proportions of the various hepatocytes are fairly constant between livers, some hepatocyte types may be underrepresented or sporadically represented in cells recovered by the traditional methods, which might not perfuse all of the lobes to a significant extent. The new methods can perfuse all of the lobes more thoroughly, and they can therefore be expected to yield more consistent results, representative of the heterogeneous hepatocyte population.

Other features and advantages of the invention will be apparent from the following detailed description, and from the claims.

BRIEF DESCRIPTION OF THE DRAWING

FIG. 1 is a schematic representation of the functional anatomy of a liver.

DETAILED DESCRIPTION OF THE INVENTION

Standard organ perfusion methods do not seem adequate for thorough perfusion, often leaving large portions of lobes of the organ intact. As a result, the recovery of cells from the organ is typically significantly lower than is theoretically possible (i.e., based on the number of cells that are contained in the fully intact organ). By increasing perfusion flow rate, occluding at least one major blood vessel leading out of the organ, increasing enzymatic digestion time, and using vigorous tissue dissociation techniques, a uniquely high yield of viable cells can be achieved.

A typical procedure for practicing the new methods entails some or all of the following steps, or variations thereupon, although other equivalent procedures are also contemplated within the scope of the invention.

Preparation of the Perfusion Buffers

Blanching buffer: Commercially available blanching buffers are used. For example, Abbott Lactated Ringers Solution (Medical Specialties, South Easton, Mass., cat# AB7953-09) is suitable.

Transport buffer: Commercially available transport buffers, such as Viaspan™ (DuPont, Wilmington, Del., NDC# 1000-0046-06), can be used.

Alternatively, the transport buffer can be prepared according to, for example, the University of Wisconsin-D buffer (UW-D) protocol (see, for example, *Transplantation*, 48:1–5, 1989). To prepare 10 L of UW-D transport buffer working solution, 178.3 g raffinose, 12.3 g magnesium sulfate heptahydrate, 9.2 g glutathione, and 1.36 g allopurinol (dissolved in 20 ml 1 N sodium hydroxide) are combined. A 1 L solution of 358.3 g lactobionic acid adjusted to pH 7.1 is added. 34.0 g monobasic potassium phosphate is added. Sufficient McGaw Water for Injection (WFI; purchased, e.g., from Medical Specialties, South Easton, Mass., cat# MGL8500) is added to bring the total volume to 10 L. Finally, the pH is adjusted to 7.25 with 1 N sodium hydroxide.

Chelating buffer: 10 L of a 10× stock solution of EDTA chelating buffer is prepared as follows: 210 g sodium bicarbonate, 818 g sodium chloride, 37.3 g potassium chloride, 19.7 g magnesium sulfate heptahydrate, 22.7 g dibasic sodium phosphate, 5.4 g monobasic potassium phosphate, and 58.4 g ethylenediaminetetraacetic acid (EDTA) are dissolved in sufficient WFI to bring the total volume to 10 L.

Prior to use, the stock solution is diluted 10 to 1. The resulting 1× working buffer is adjusted to pH 7.25 with 1 N aqueous sodium hydroxide. 12.5 ml of gentamicin sulfate is also added per 10 l of buffer.

Digestion buffer: 10 L of a 1× working solution of 0.05% collagenase digestion buffer is prepared as follows: 2.2 g potassium chloride, 75.9 g sodium chloride, 1.4 g monobasic sodium phosphate monohydrate, 18.1 g dextrose, 23.8 g 4-(2-hydroxyethyl)-1-piperazineethanesulfonic acid (HEPES), and 2.7 g calcium chloride are dissolved in sufficient WFI to bring the total volume to 10 L. The pH is adjusted to 7.25 with 1 N aqueous sodium hydroxide, and 0.5 to 1.25 g of collagenase (depending on enzyme activity) is added per liter of the resulting solution.

Preparation of the Animal

To aid in exsanguination, 1.5 to 2.5 ml of heparin (i.e., about 120 IU of injectable grade heparin per pound of donor body weight) is injected into the animal prior to surgery. Heparin is an anticoagulating agent that prevents the formation of blood clots that can clog or block blood vessels. An incision is made in the animal and a major vein leading from the organ of interest is dissected and cannulated. For example, the portal vein of the liver can be cannulated and the vena cava of the liver left open. The remaining blood vessels leading to or from the organ are tied off, or occluded, and the organ is removed from the animal. The vena cava on the cranial side of the liver is tied off when the liver is ex vivo.

Perfusion of the Organ

The organ is perfused with blanching buffer chilled to 4° C., using the cannulated vessel as an input tube and, in the case of a liver, the caudal vena cava as an output tube. The flow rate for perfusion with the blanching buffer is typically about 6 ml/min per pound of the host's body weight, but not less than about 200 ml/min. A single pass perfusion volume of 1 liter is generally sufficient for blanching.

The blanching buffer rapidly clears the blood from the organ, thereby reducing the likelihood of clotting within the organ. Whenever a blood clot forms in a vessel, it closes off access to that part of the organ which the vessel normally supplies with blood. It is then difficult or even impossible to perfuse that part of the organ with any of the perfusates used in the isolation process; one goal of the process is to access as much of the organ as possible by using the vascular system that exists within each organ.

During the perfusion process, the opened vessel can be blocked off temporarily, causing inflation of the organ and increasing the pressure within the organ. This must be done very carefully so that the vessels do not burst. The blockage can be repeated multiple time during the perfusion with the blanching buffer, as well as with the other buffers.

While the organ is not inflated, the various lobes of the organ can be manually massaged to promote thorough clearing of the blood from the organ. Massaging can also help to break apart any nascent clots.

Perfusion of the organ with chilled transport buffer is begun as soon as possible following perfusion with the blanching buffer to reduce warm ischemia time; the transport buffer preserves the organ while it is transported, for example, from the operating room to the cell isolation laboratory. The transport buffer is introduced at a flow rate of about 1–3 ml/min per gram of the organ's mass. The mass of the organ can be estimated, if necessary. A flow time of 2 minutes is usually suitable for filling most organs with transport buffer. Provided that the blanching buffer was successful in removing the blood from, and preventing clots in, all lobes of the organ, the transport buffer can perfuse all of the lobes and preserve the cells within them. The organ can be kept viable for 10 hours when filled with the transport buffer.

When the organ has been brought to the site where the cell isolation is to be performed, the transport buffer is replaced by a chelating buffer. Chelators, such as EDTA, promote the separation of the cells adhered within the organ. EDTA removes calcium ions that are crucial for cell adhesion. Again, a flow rate of about 1–3 ml/min per gram of organ, for 10–30 minutes, is appropriate.

Finally, the organ is perfused by the digestion buffer. The enzymes in the digestion buffer (e.g., collagenase) break down the intercellular networks which maintain the integrity of the organ. Perfusion with digestion buffer is continued until the organ has lost its shape and has become amorphous. This typically requires a flow rate of 1–3 ml/min per gram of organ mass for about 10 to 60 minutes, depending on the size of the organ.

Isolation of the Cells

The organ is cooled in Dulbecco's Modified Eagle Medium (DMEM) with 10% bovine calf serum at 4° C. The organ is broken up initially by the finger fracture technique, also called manual dissociation. The organ is crushed and broken into small pieces by hand, then poured into a sieve. The sieve can be lined with one or more layers of glass, metal, or plastic beads of various shapes and sizes to help further dissociate the cells from the intercellular materials. The beads also help break up any lobes that did not fall apart during the perfusion with digestion buffer. Additionally, sieves having different mesh sizes can be employed if it is desirable to break apart small clusters of cells. The cells that pass through the sieves can be collected and stored over ice. The cells can also be washed with additional medium, such as DMEM Complete.

The invention will be further described in the following example, which does not limit the scope of the invention described in the claims.

EXAMPLE

Livers were procured from 6–8 week old pigs weighing 8.0 to 22.3 kg. Prior to surgery, approximately 1.5 ml of heparin was injected intravenously into each pig. The numerals in the following text refer to the schematic representation of the functional anatomy of a liver in FIG. 1.

The portal vein 12 of each liver 10 was dissected and cannulated. The liver 10 was then perfused with three liters of cold lactated ringers buffer (Medical Specialties, South Easton, Mass., cat# AB7953-09), at a flow rate (in ml/min) equal to about 6 times the body weight of the pig (in lbs), but not less than about 200 ml/min.

The lobes 14 of the liver were manually massaged during the perfusion with the blanching, transport, chelating, and digestion buffers.

The livers 10 were subjected to a 1.5 ml/min/(g of liver) flow rate of cold Viaspan® (Dupont, Wilmington, Del.) transport buffer immediately after procurement.

The cranial vena cava 16 was completely occluded by either manual or surgical ligation. Occlusion of the cranial vena cava 16 increases the pressure in the liver 10, thereby forcing efferent flow into all lobes 14 of the liver and out through the caudal vena cava 18. Additionally, the caudal vena cava 18 was momentarily pinched closed periodically during the perfusion with each buffer so that the liver 10 would become more fully engorged as the perfusate reached all parts of the lobes 14. This was meant to open up the vascular network of the liver 10, making it more accessible to EDTA and collagenase perfusion.

Two liters of 1× EDTA buffer were warmed to 37° C. and pumped through the liver 10 via the portal vein 12 at a flow rate equal to 1.5 milliliters/minute/gram of liver.

The liver 10 was perfused with collagenase buffer (800 PZ units/liter buffer) at a flow rate equal to 1.5 milliliters/minute/gram of liver, for approximately 30 minutes, or until the integrity of the organ had been lost. The liver 10 was then cooled down with DMEM Complete media (4° C.) and the tissue was dissociated using a finger fracture technique.

Media and tissue were then poured through three sieves, having mesh sizes of 425 μm, 212 μm, and 106 μm, respectively. The sieves each contained a layer of beads which helped to further dissociate the liver tissue. The beads help break up any part of any lobe 14 which does not fall apart during collagenase perfusion. The resulting cell suspension was collected in two bags kept on ice. The cells were washed with more DMEM Complete media using Cobe 2991 Cell Processors. Traces of collagenase and cell debris were removed from the cell suspension. Hepatocytes were assessed for viability using Trypan blue and counted for total yield.

The average yield of 17 isolations using this procedure equals 52 billion viable cells per liver.

OTHER EMBODIMENTS

It is to be understood that while the invention has been described in conjunction with the detailed description thereof, that the foregoing description is intended to illustrate and not to limit the scope of the appended claims. Other aspects, advantages, and modifications are within the scope of the following claims.

What is claimed is:

1. A method of collecting cells from a mammalian organ, wherein said organ has a major blood vessel leading to said organ, the method comprising:

cannulating said blood vessel to produce an input line for the introduction of a fluid;

occluding all but one remaining blood vessel leading to or from said organ, such that the non-occluded vessel constitutes an output line for the egress of said fluid;

digesting said organ with a continuous flow of collagenase buffer in through said input line and out through said output line;

dissociating said digested organ; and placing said dissociated organ on a sieve, wherein said sieve contains a layer of beads to separate said cells from the remainder of said organ.

2. The method of claim 1, wherein said cells are hepatocytes and said mammalian organ is a liver.

3. The method of claim 2, wherein said cells are porcine hepatocytes and said mammalian organ is a porcine liver.

4. A method of collecting cells from a mammalian organ, wherein said organ has a major blood vessel leading to said organ, the method comprising:

cannulating said blood vessel to produce an input line for the introduction of fluids;

occluding all but one remaining blood vessel leading to or from said organ, such that the non-occluded vessel constitutes an output line for the egress of said fluids;

digesting said organ with a continuous flow of collagenase buffer introduced via said input line and evacuated via said output line;

massaging said organ concurrent with said digesting step to enhance perfusion;

dissociating said digested organ; and passing said dissociated organ through a sieve to separate said cells from the connective tissue of said organ.

5. The method of claim 4, wherein said cells are hepatocytes and said mammalian organ is a liver.

6. The method of claim 5, wherein said cells are porcine hepatocytes and said mammalian organ is a porcine liver.

7. The method of claim 4, wherein said sieve contains a layer of beads.

8. The method of claim 7, wherein said cells are hepatocytes and said mammalian organ is a liver.

9. The method of claim 8, wherein said cells are porcine hepatocytes and said mammalian organ is a porcine liver.

10. A method of collecting cells from a mammalian organ, wherein said organ has a major blood vessel leading to said organ, the method comprising:

cannulating said blood vessel to produce an input line for the introduction of fluids;

occluding all but one remaining blood vessel leading to or from said organ, such that the non-occluded vessel constitutes an output line for the egress of said fluids;

digesting said organ with a continuous flow of collagenase buffer introduced via said input line and evacuated via said output line;

periodically and momentarily blocking said output line during said digesting step to increase the pressure within said organ;

manually dissociating said digested organ; and passing said crushed organ through a sieve to separate said cells from the connective tissue of said organ.

11. The method of claim 10, wherein said cells are hepatocytes and said mammalian organ is a liver.

12. The method of claim 11, wherein said cells are porcine hepatocytes and said mammalian organ is a porcine liver.

13. The method of claim 10, wherein said method further comprises massaging said organ concurrent with said digesting step to enhance perfusion.

14. The method of claim 13, wherein said cells are hepatocytes and said mammalian organ is a liver.

15. The method of claim 14, wherein said cells are porcine hepatocytes and said mammalian organ is a porcine liver.

16. The method of claim 10, wherein said sieve contains a layer of beads.

17. The method of claim 16, wherein said cells are hepatocytes and said mammalian organ is a liver.

18. The method of claim 17, wherein said cells are porcine hepatocytes and said mammalian organ is a porcine liver.

19. The method of claim 16, wherein said method further comprises massaging said organ concurrent with said digesting step to enhance perfusion.

20. The method of claim 19, wherein said cells are hepatocytes and said mammalian organ is a liver.

21. The method of claim 20, wherein said cells are porcine hepatocytes and said mammalian organ is a porcine liver.

* * * * *